US011111358B2

(12) United States Patent
Pollino et al.

(10) Patent No.: US 11,111,358 B2
(45) Date of Patent: Sep. 7, 2021

(54) STABILIZER COMPOUNDS

(71) Applicant: SOLVAY SPECIALTY POLYMERS USA, LLC, Alpharetta, GA (US)

(72) Inventors: Joel Pollino, John Creeks, GA (US); Gregory Goschy, Atlanta, GA (US); Satchit Srinivasan, Dallas, TX (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 92 days.

(21) Appl. No.: 16/710,469

(22) Filed: Dec. 11, 2019

(65) Prior Publication Data

US 2020/0157312 A1 May 21, 2020

Related U.S. Application Data

(63) Continuation of application No. 15/312,752, filed as application No. PCT/EP2015/061080 on May 20, 2015, now abandoned.

(60) Provisional application No. 62/001,336, filed on May 21, 2014.

(51) Int. Cl.
| | | |
|---|---|---|
| *C07D 211/46* | (2006.01) | |
| *C08K 5/43* | (2006.01) | |
| *C08K 5/3435* | (2006.01) | |

(52) U.S. Cl.
CPC .......... *C08K 5/3435* (2013.01); *C07D 211/46* (2013.01); *C08K 5/43* (2013.01)

(58) Field of Classification Search
CPC ....... C07D 211/46; C08K 5/43; C08K 5/3435
USPC ....................................................... 524/609
See application file for complete search history.

(56) References Cited

U.S. PATENT DOCUMENTS

| | | | |
|---|---|---|---|
| 3,904,581 A | 9/1975 | Murayama et al. | |
| 4,049,647 A | 9/1977 | Holt et al. | |
| 5,030,243 A | 7/1991 | Reinert | |
| 5,438,142 A * | 8/1995 | Fritsch | C07C 37/20 546/240 |
| 5,976,417 A | 11/1999 | Bechtold et al. | |
| 2006/0079610 A1 | 4/2006 | Staniek | |
| 2007/0167487 A1 * | 7/2007 | Peters | A61P 25/00 514/317 |
| 2008/0146737 A1 | 6/2008 | Ashiura et al. | |
| 2009/0233910 A1 | 9/2009 | Botez et al. | |

FOREIGN PATENT DOCUMENTS

| | | |
|---|---|---|
| DE | 4000551 A1 | 7/1990 |
| DE | 4141661 A1 | 7/1992 |
| EP | 1449872 A1 | 8/2004 |
| WO | 2004076419 A1 | 9/2004 |
| WO | 2005123679 A2 | 12/2005 |
| WO | 2006108965 A2 | 10/2006 |
| WO | 2014206344 A1 | 12/2014 |

OTHER PUBLICATIONS

Bojinov et al. [Synthesis and photophysical investigations of novel combined benzo[de]anthracen-7-one/2,2,6,6-tetramethylpiperidines as fluorescent stabilisers for polymer materials. Polymer Degradation and Stability, 85(2), 789-797(2004)).
U.S. Appl. No. 16/711,050, Joel Pollino, filed Dec. 11, 2019.

* cited by examiner

*Primary Examiner* — Kelechi C Egwim

(57) ABSTRACT

A piperidine-based stabilizer compound of formula (I) or (II) that imparts UV, thermal, and/or thermo-oxidative stability to polymer compositions and more specifically to aromatic polymers and polymer compositions thereof.

15 Claims, No Drawings

STABILIZER COMPOUNDS

CROSS REFERENCES TO RELATED APPLICATIONS

This application claims priority to U.S. provisional patent application No. 62/001,336, filed on May 21, 2014 and incorporated herein by reference.

TECHNICAL FIELD

The present invention describes the use and synthesis of new piperidine-based stabilizer compounds (SC), which provide UV, thermal, and thermo-oxidative stability to polymers.

BACKGROUND

High performance aromatic polymers feature, because of their very high glass transition temperatures and/or melting temperatures, excellent properties including outstanding heat resistance. Aromatic polysulfones and polyetherketones are, for example, widely used in applications where their strength, resistance to harsh chemicals and to high temperatures is necessary.

Unfortunately, many natural and synthetic polymers such as the above mentioned high performance aromatic polymers are prone to light absorption and are attacked by UV radiation. As a result, they undergo oxidation, chain scission, uncontrolled radical recombination and cross-linking reactions. This phenomenon, known as UV degradation, is usually catalyzed in high heat environments in the presence of oxygen. The UV degradation of polymers can affect a material's mechanical properties, produce discoloration and fading, roughen the surface, decrease tensile strength, and reduce their overall life time performance.

A wide range of light and heat stabilizers for polymers are known and have been used alone or in various combinations to prevent or retard the kinetics of polymer degradation that is initiated by exposure to light and heat. The effectiveness of stabilizers to defend a material against UV radiation and heat depends on several factors including; the intrinsic efficacy of the stabilizer, its concentration, and its solubility in a particular polymer matrix, as well as how well it is distributed in the matrix. Intrinsic volatility of the stabilizer is also an important factor to consider when working with materials which are processed at high temperatures as it may lower the concentration of the stabilizer in a particular polymer matrix as a result of evaporation during processing and subsequent use.

Heat stabilizers have been used for many years in various polymer matrixes. Common types of heat stabilization packages include organophosphites, used as a short-term antioxidant to protect the polymer from the high temperature and high shear, and/or phenolic antioxidants used for long-term protection.

Over the past century, a number of light stabilizer compounds have also been developed and commercialized as additives tailored to retard or eliminate photo-initiated oxidative processes. These additives are generally categorized into one of 4 classes: UV absorbers, excited state quenchers, radical scavengers, and peroxide decomposers. Certain derivatives of 2,2,6,6-tetramethyl piperidine, also known as hindered amine light stabilizers (HALS), have been known for a long time to improve the light stability, aging properties, and extended field life of polymeric compositions. For example, U.S. Pat. No. 4,049,647 discloses their use in low melting temperature polymeric materials such as polyolefins, aliphatic polyamides and polystyrene.

Nearly all commercially available heat and light stabilizers are indeed well suited for blending with low melting temperature commodity polymers requiring low process temperatures (i.e. below 250° C.).

However, such commercial heat and light stabilizers are generally poorly suited for high performance aromatic polymers where process temperatures are substantially more intense (i.e. above 250° C.), owing to the highly aliphatic character of most commercial stabilizing compounds, which is prone to thermo-oxidative decomposition upon exposure temperatures above 200° C.

Additionally, the Applicant has found that, upon blending many commercial heat and light stabilizers with high performance aromatic polymers, a disastrous reduction in the thermal properties of such systems occurs, especially with respect to a detrimental lowering of the glass transition temperature, which in turn diminishes the high temperature mechanical performance of such polymeric engineering materials.

There exists a need, therefore, to identify and develop stabilizer compounds that are well suited for high performance aromatic polymers in that they possess good inherent thermal-oxidative stability and impart good light stability, while also maintaining the glass transition temperature of the polymer(s) they are blended with so to preserve the high temperature mechanical performance of such materials.

SUMMARY

The present invention relates to stabilizer compounds (SC) of formula (I) or formula (II):

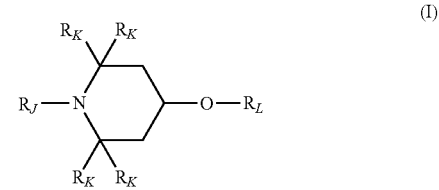

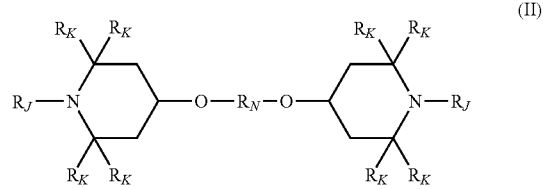

wherein $R_J$ is selected from the group consisting of —H, aliphatic groups and alkoxy groups, and wherein each of $R_K$, equal to or different from each other and from $R_J$, is selected from aliphatic groups, and wherein $R_L$ is a monovalent substituent selected from the group consisting of:

a group of general formula (Y-I):

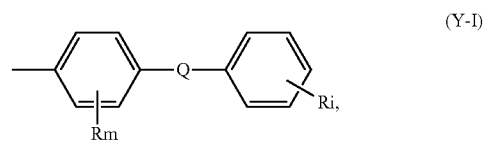

and
a group of general formula (Y-II):

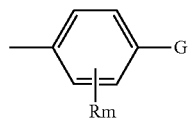
(Y-II)

wherein Ri and Rm are the same or different from each other and are independently selected from the group consisting of —H, —CF$_3$, —CN, —C(=O)NH$_2$, —NO$_2$, alkyl groups, perfluorinated groups, aryl groups, aryl amine groups, aryl ether groups, aryl sulfone groups, aryl thioether groups, fused aryl ring systems, sulfonic acids, carboxylic acids, phosphonic acids, sulfonic acid salts, carboxylic acid salts, and phosphonic acid salts, and
wherein Ri is either in an ortho, meta or para position, and wherein Rm is either in an ortho or meta position, and
wherein Q is selected from the group consisting of a bond, —O—, —CH$_2$—, —C(CH$_3$)$_2$—, —NH—, —S—, —C(CF$_3$)$_2$—, —C(=CCl$_2$)—, and —SO$_2$—, and
wherein G is a group selected from the group consisting of —C(=O)NH$_2$, —NO$_2$, alkyl groups, perfluorinated groups, aryl groups, aryl amine groups, aryl ether groups, aryl sulfone groups, aryl thioether groups, fused aryl ring systems, sulfonic acids, carboxylic acids, phosphonic acids, sulfonic acid salts, carboxylic acid salts, and phosphonic acid salts,
wherein R$_N$ is a divalent substituent selected from the group consisting of:
a group of general formula (Z-I):

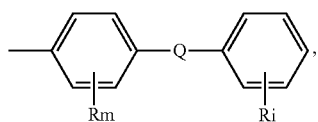
(Z-I)

and
a group of general formula (Z-II):

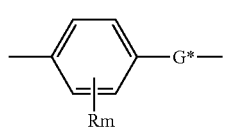
(Z-II)

wherein Ri and Rm are the same or different from each other and are independently selected from the group consisting of —H, —CF$_3$, —C(=O)NH$_2$,
—NO$_2$, alkyl groups, perfluorinated groups, aryl groups, aryl amine groups, aryl ether groups, aryl sulfone groups, aryl thioether groups, fused aryl ring systems, sulfonic acids, carboxylic acids, phosphonic acids, sulfonic acid salts, carboxylic acid salts, and phosphonic acid salts,
wherein Ri and Rm are independently either in an ortho or meta position, and
wherein Q is as above described and
wherein G* is a divalent group selected from the group consisting of alkyl groups, perfluorinated groups, aryl groups, aryl amine groups, aryl ether groups, aryl sulfone groups, aryl thioether groups, and fused aryl ring systems.

Another aspect of the present invention relates to two distinct methods for the manufacture of said stabilizer compounds (SC).

Still another aspect of the present invention relates to a polymer composition (P) comprising said at least one stabilizer compound (SC) and at least one polymer and to a method for stabilizing a polymer comprising the addition of at least one stabilizing compound (SC) to at least one polymer.

Yet another aspect of the present invention is directed to an article comprising said polymer composition (P).

DETAILED DESCRIPTION OF THE INVENTION

The Applicant has discovered that stabilizer compounds (SC) of formula (I) or formula (II):

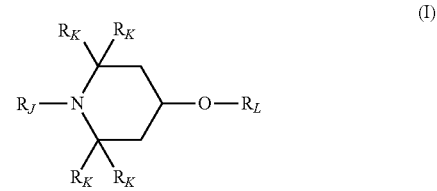
(I)

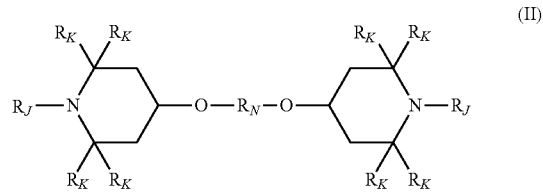
(II)

wherein R$_J$, R$_K$, R$_L$ and R$_N$ are as above described, imparts high performance aromatic polymers compositions with good heat and light resistance, while surprisingly maintaining their glass transition temperatures to a very high level.

In the formulas (I) and (II), R$_J$ can be a —H, or a branched, linear or cyclic aliphatic groups or alkoxy groups. Non-limitive Examples of R$_J$ are notably —H, —CH$_3$, —CH$_2$CH$_3$, —(CH$_2$)$_5$CH$_3$, —(CH$_2$)$_7$CH$_3$, —(CH$_2$)$_2$O CH$_3$, —OCH$_3$, —O(CH$_2$)$_5$CH$_3$, —O(CH$_2$)$_7$CH$_3$,

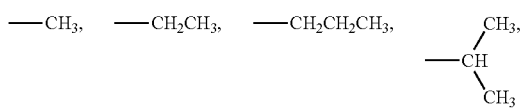

R$_J$ is preferably selected from the group consisting of —H, —CH$_3$, —CH$_2$CH$_3$, —OCH$_3$, and —OCH$_2$CH$_3$. Most preferably, R$_J$ is —CH$_3$.

In the formulaes (I) and (II), each of R$_K$, equal to or different from each other and from R$_J$, can be any branched, linear or cyclic aliphatic groups. Non-limiting examples of R$_K$ are notably:

—CH$_3$,   —CH$_2$CH$_3$,   —CH$_2$CH$_2$CH$_3$,   —CH(CH$_3$)$_2$

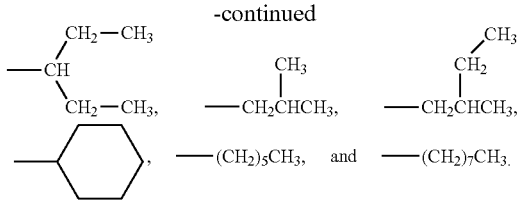
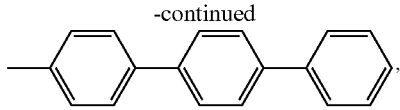

$R_K$ is preferably selected from the group consisting of —CH$_3$, and —CH$_2$CH$_3$.

In the same formula (I), $R_L$ is a monovalent substituent selected from the group consisting of a group of general formula (Y-I) and (Y-II), as above defined.

In formulae (Y-I) and (Y-II), Ri may be in an ortho, meta or para position, and Rm may be in an ortho or meta position. Ri is preferably in a para position. Ri and Rm are preferably —H.

In formula (Y-I), Q is preferably —SO$_2$—.
In formula (Y-II), G is preferably —C(=O)NH$_2$.
In the formula (II), $R_N$ is a divalent substituent selected from the group consisting of a group of general formula (Z-I) and (Z-II), as above defined.

Non-Limiting examples of Ri and Rm are notably:
Alkyl Groups: —CH$_3$, —CH$_2$—O—CH$_3$,

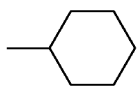

Perfluorinated Groups: —CF$_3$, —CH$_2$ (CF$_2$)$_5$CF$_3$,
Aryl Groups:

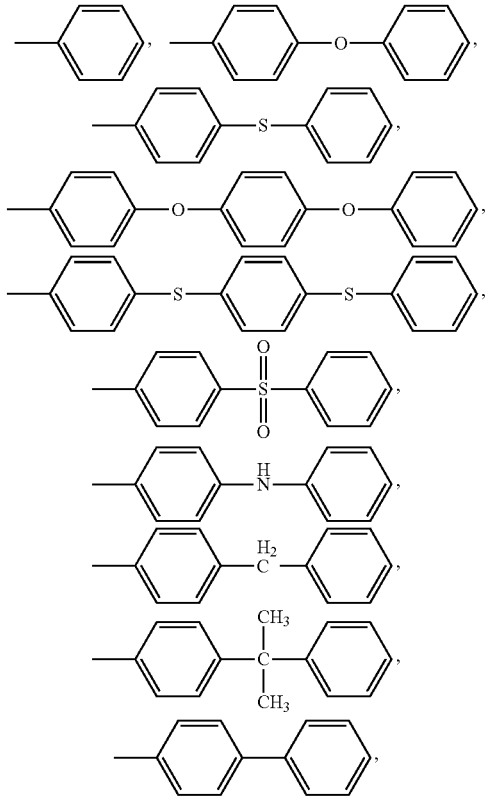

Aryl Amine Groups:

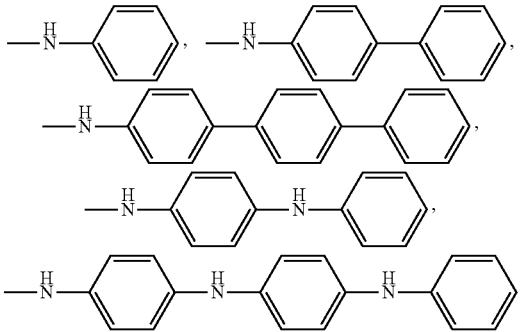

Aryl Ether Groups:

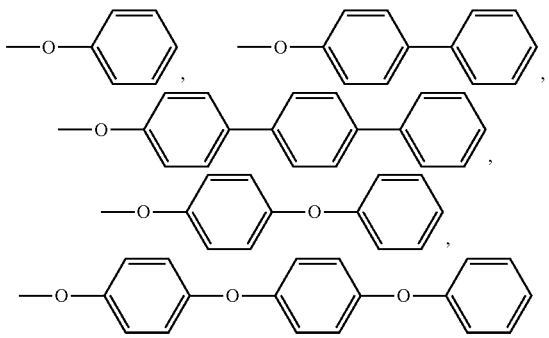

Aryl Sulfone Groups

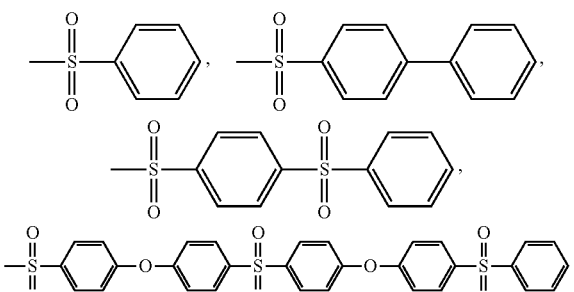

Aryl Thioether Groups:

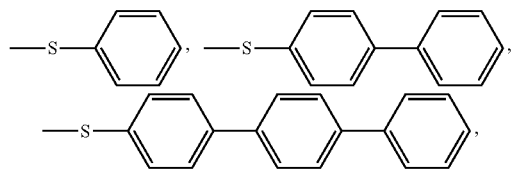

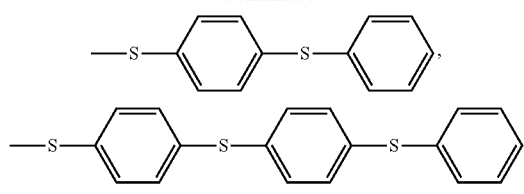

Fused aryl ring systems:

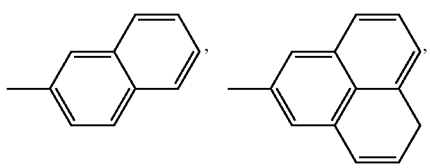

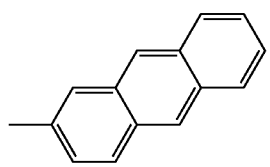

In formula (Z-I), Q is as above described for formula (Y-I). It is preferably a bond or —SO$_2$—.

In formula (Z-II), G* may be selected from the group consisting of alkyl groups, perfluorinated groups, aryl groups, aryl amine groups, aryl ether groups, aryl sulfone groups, aryl thioether groups, fused aryl ring systems.

In a first embodiment, the stabilizer compounds (SC) of formula (I) are preferably selected from the group consisting of structures (A-A) to (A-C) herein below:

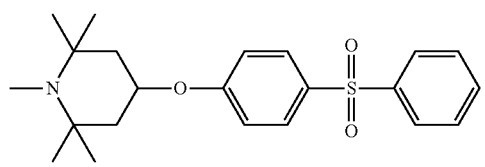

(A-A)

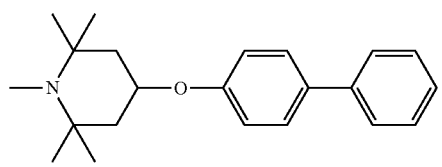

(A-B)

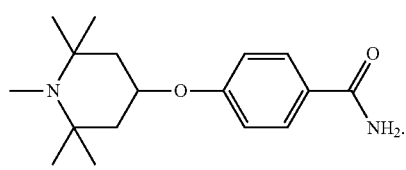

(A-C)

In a second embodiment, the stabilizer compounds (SC) of formula (II) are preferably selected from the group consisting of structures (B-A) to (B-B) herein below:

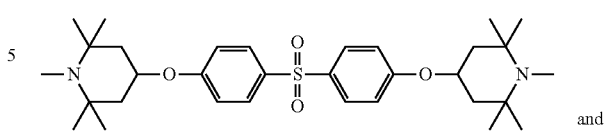

(B-A)

and

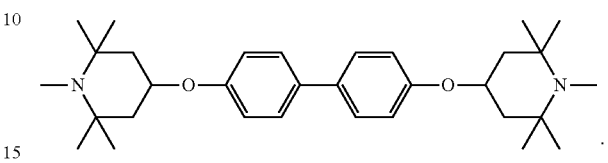

(B-B)

Various stabilizer compounds (SC) of the two formulae (I) and (II) were synthesized in the laboratory with high yields (65-85%).

Therefore, another aspect of the present invention is directed to a method for the manufacture of the stabilizer compound of formula (I), comprising the step of reacting compounds of formulae (III) and (IV) together in the presence of a base,

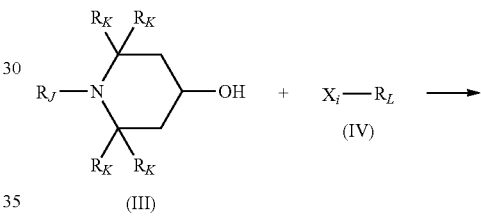

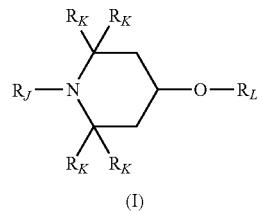

(I)

wherein $X_i$ is a halogen selected from the group consisting of chlorine, fluorine, bromine, and iodine, and wherein $R_J$, $R_K$, $R_L$ are as defined above for formula (I). $X_i$ is preferably selected from the group consisting of chlorine and fluorine.

Here, the compounds of formula (IV) possess preferably an electron withdrawing group para to the halogen Xi.

Still another aspect of the present invention is directed to a method for the manufacture of the stabilizer compound of formula (II), comprising the step of reacting compounds of formulae (III) and (IV) together in the presence of a base,

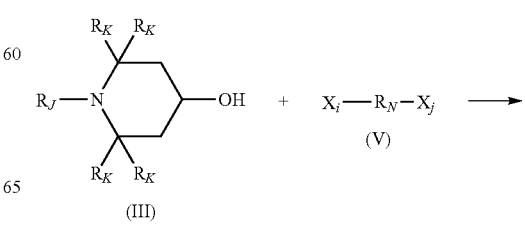

-continued

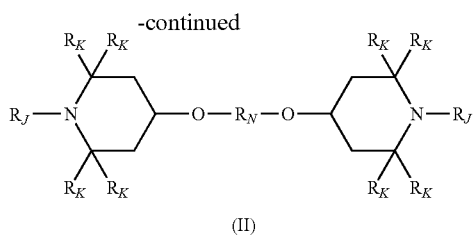

(II)

wherein $X_i$ or $X_j$ are the same or independently selected halogens from the group consisting of chlorine, fluorine, bromine, and iodine, and wherein $R_J$, $R_K$, $R_N$ are as defined above for formula (II). Xi is preferably selected from the group consisting of chlorine and fluorine.

In the methods for the manufacture of the stabilizer compounds of formula (I) or (II), the reaction is preferably carried out in a polar aprotic solvent. Any polar aprotic solvent that is capable of dissolving the two starting materials (i.e. compounds of formulae (III) and (IV) or (III) and (V)) can be used in the disclosed methods. The polar aprotic solvent is preferably selected from tetrahydrofuran (THF) or N-methylpyrrolidone (NMP).

The reaction temperature can be any temperature up to the boiling point of the solvent, while the lower temperatures usually lead to slower kinetic rates of the reaction(s). If the solvent used is THF, then the reaction is preferably carried out at a temperature of between 25° C. and 66° C. at atmospheric pressure, more preferably between 40 and 66° C. and most preferably between 55 and 66° C. If the solvent used is N-methylpyrrolidone, then the reaction is preferably carried out at a temperature of between 25° C. and 204° C. at atmospheric pressure, more preferably between 50 and 150° C. and most preferably between 80 and 120° C. Excellent results were obtained when the reaction was carried out at a temperature of 66° C. at atmospheric pressure when the solvent used was THF, and 100° C. at atmospheric pressure when the solvent used was NMP.

The steps of reacting compounds of formulae (III) and (IV) or compounds of formulae (III) and (V) in the above disclosed methods for the manufacture of the stabilizer compounds of formula (I) or (II), are preferably carried out in the presence of a base capable of deprotonating a secondary alcohol, and preferably having a pKa of at least 16. The base can be added to compound of formula (III) alone or to a mixture of compounds of formulae (III) and (IV). The base is most preferably the potassium tert-butoxide.

To prepare the desired stabilizer compounds (SC) of the general formula (I) shown above, one of two general synthesis procedures were carried out. Specifically, in a first embodiment, the first general procedure was utilized when para-substitution with an electron withdrawing group, $R_L$, as given above (i.e. $SO_2$, $CF_3$, CN, etc) allowed for the reaction to proceed toward completion and produce high yields aided by utilizing reflux with THF as the polar aprotic solvent.

In a second embodiment, the second general procedure was preferably used when there was an absence of an electron withdrawing group, where the use of a higher boiling and more polar aprotic solvent lead to higher yields and/or lower reaction times.

The synthesis of both stabilizer compounds (SC) of formulae (I) and (II) respectively—resulted in the formation of the desired products. Relative yields depended strongly upon the activity of the reactants and to a lesser extent the degree of substitution. Inactivated halogenated reactants, such as fluorobenzene, 4-fluorobiphenyl, and the 4,4'-difluoro-biphenyl were substantially less reactive than activated halogenated reactants such as 4,4'-dichloro diphenyl sulfone, 4-chloro diphenyl sulfone, 4,4'-difluoro benzophenone, and 4-fluoro benzophenone. Such inactive halogenated reactants necessitated use of the more polar solvent (NMP) and higher reaction temperatures (100° C.). These stabilizer compounds (SC) were then blended to several polymers to evaluate their light and thermal stabilizing effect.

Thus, another aspect of the present invention relates to a polymer composition (P), comprising at least one of the above disclosed stabilizer compounds (SC) and at least one polymer. The polymers of the polymer composition (P) are high performance aromatic polymers comprising advantageously more than 35 mol %, preferably more than 45 mol %, more preferably more than 55 mol %, still more preferably more than 65 mol % and most preferably more than 75 mol % of recurring units which are aromatic recurring units. For the purpose of the present invention, the expression "aromatic recurring unit" is intended to denote any recurring unit that comprises at least one aromatic group in the main polymer backbone.

The polymer of the polymer composition (P) may be a semi-crystalline polymer or an amorphous polymer. Semi-crystalline polymers may typically have glass transition temperatures of at least 120° C., preferably at least 140° C. and melting temperatures generally greater than 250° C., preferably greater than 300° C.

Amorphous polymers typically have a glass transition temperature of at least 140° C., more typically of at least 150° C. and up to 200° C. Glass transition temperature (Tg) and melting temperature (Tm) are generally determined by DSC, according to ASTM D3418.

The polymer of the polymer composition (P) may be selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene, styrene acrylonitrile, acrylate styrene acrylonitrile, cellulosic acetate butyrate, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

Among the more preferred polymers, one may cite the aromatic poly(sulfone)s, aromatic poly(ether ketone)s such as poly(ether ether ketone)s (PEEK), aromatic poly(amide)s, aromatic poly(imide)s, poly(phenylene)s, and aromatic liquid crystalline polymers.

Aromatic poly(sulfone)s include notably polyphenylsulfone, polysulfone, polyethersulfone, and polyetherethersulfone, the structural repeat units of which are listed below:

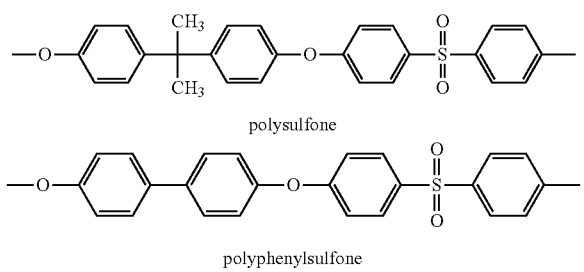

polysulfone polyphenylsulfone

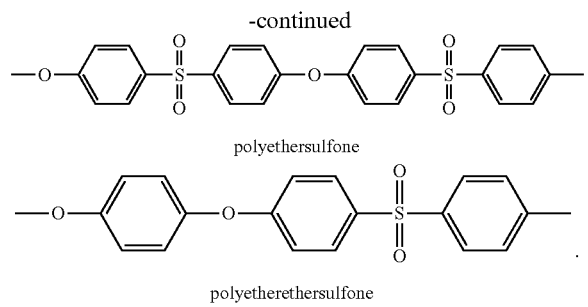

polyethersulfone polyetherethersulfone

Aromatic poly(ether ketone)s include notably poly(ether-ketone), poly(etheretherketone) and poly(etherketoneketone), the structural repeat units of which are listed below:

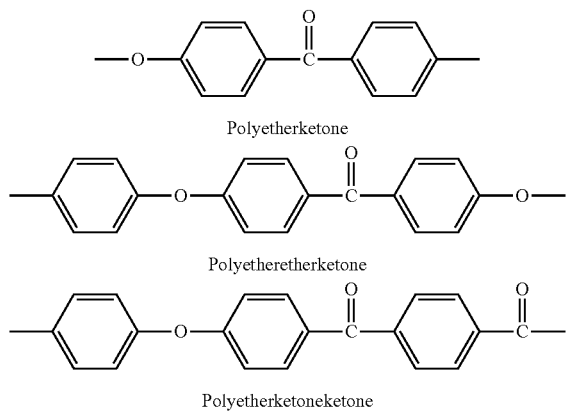

Polyetherketone

Polyetheretherketone

Polyetherketoneketone

The polymer composition (P) may also further comprises at least another ingredient selected from the group consisting of dyes, pigments, fillers, UV stabilizers, light stabilizers, optical brighteners.

The polymer composition (P) comprises advantageously at least 0.01 wt. %, preferably at least 1.0 wt. %, more preferably at least 1.5 wt. %, still more preferably at least 2.0 wt. % and most preferably at least 2.5 wt. % of the stabilizer compounds (SC). Also, the polymer composition (P) comprises advantageously at most 10 wt. %, preferably at most 9 wt. %, more preferably at most 8 wt. %, still more preferably at most 6 wt. % and most preferably at most 5 wt. % of the stabilizer compounds (SC).

When no other ingredient than the stabilizer compounds (SC) and the at least one polymer are present, the polymer composition (P) comprises advantageously at least 20 wt. %, preferably at least 30 wt. %, more preferably at least 40 wt. %, still more preferably at least 50 wt. % and most preferably at least 60 wt. % of the at least one polymer. Also, the polymer composition (P) comprises advantageously at most 99.99 wt. %, preferably at most 99.95 wt. %, more preferably at most 99.90 wt. %, still more preferably at most 99.5 wt. % and most preferably at most 99 wt. % of the at least one polymer.

The polymer composition (P) may further comprise at least one additional stabilizer selected from the group consisting of 2-(2'-hydroxyphenyl)benzotriazoles, oxamides, 2-(2-hydroxyphenyl)1,3,5-triazines, 2-hydroxybenzophenones, cyanoacrylates, benzo-oxazolines, and hindered phenolic antioxidants.

It may be advantageous to further incorporate in the polymer composition (P) additional hindered amine light stabilizers ("HALS"). Examples of such HALS are (2,2,6,6-tetramethylpiperidyl) sebacate, (2,2,6,6-tetramethylpiperidyl-) succinate, condensate of 1-hydroxyethyl-2,2,6,6-tetramethyl-4-hydroxypiperidine and succinic acid, condensate of N,N'-bis(2,2,6,6-tetramethyl-1-4-piperidyl) hexamethylene diamine and 4-tert-octylamino-2,6-dichloro-1,3,-5-s-triazine, tris(2,2,6,6-tetramethyl-4-piperidyl) nitrilotriacetate, tetrakis(2,2,6,6-tetramethyl-4-piperidyl) 1,2,3,4 butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethyl piperidine, to (1,2,2,6,6-pentamethylpiperidyl) 2-n-butyl-2 (2-hydroxy-3,5-di-tert-butylbenzyl)malonate, 3-n-octyl-7,7,9,9-tetramethyl-1,3,8-triazas-piro[4.5]decane-2,4-dione, to (1-octyloxy-2,2,6,6-tetramethylpiperidyl) sebacate, (1-octyloxy-2,2,6,6-tetramethylpiperidyl) succinate, condensate of N,N'-bis(2,2,6,6-tetramethyl-4-piperidyl) hexamethylenediamine, and compounds with similar chemical structures. As with the stabilizer compounds (SC) of the present disclosure, the HALS may be incorporated in the polymer composition (C) in conventional amounts, generally higher than 0.05 wt. % and preferably higher than 0.1 wt. %; further, these amounts are generally lower than 5 wt. % and preferably lower than 1 wt. %.

Further in accordance with the present disclosure, the polymer composition (P) may also contain a variety of other polymer additives in addition to the stabilizer compounds of the present disclosure. These additives may include fillers in spherical, spheroidal or polyhedral form, collectively known as "ingredients" herein. Among these other fillers, calcium carbonate, calcium sulfate, barium sulfate, glass beads, ceramic beads, antimony trioxide, zinc borate, and other metal salts and oxides, can be utilized.

Other optional conventional ingredients of the complete polymer composition (P) include nucleating agents such as silica, adhesion promoters, compatibilizers, curing agents, lubricants, mold release agents, dyes and colorants, smoke-suppressing agents, heat stabilizers, antioxidants, UV absorbers, tougheners such as rubbers, plasticizers, anti-static agents, melt viscosity depressants such as liquid crystalline polymers, and compounds of similar structures. The choice of fillers and other ingredients in the final polymer composition (C) including the stabilizer compounds of the present disclosure will depend primarily on the intended use for the articles of manufacture.

The components of the polymer composition (P) along with the optional additional ingredients may be incorporated into the polymer compositions (P) by a variety of different methods and procedural steps which aim to provide their collective improvement in stability properties throughout the mixture. For example, it is possible to incorporate the above mentioned components and optional additional ingredients by mixing them into the polymer at an early processing stage, or at the start or at the end of the synthesis reaction, or in a subsequent compounding process. A certain method comprises dry mixing the essential components and optional ingredients in powder or granular form, in appropriate proportions, using e.g. a mechanical blender, such as a drum blender and compounds of similar structures. The mixture is then melted batch-wise or in a continuous device, e.g. extruders and compounds of similar structures, extruding the mixture into strands and chopping the strands into pellets. The mixture to be melted may also be prepared by well-known master-batch methods. The continuous melting device may also be fed with the components and ingredients of the polymer composition (P) added separately without dry premixing. A certain other method comprises dissolving the polymer(s) in one or more organic solvents then causing the dissolved polymer(s) to precipitate by the addition of a non-solvent, and finally molding the recovered dried cake.

Of particular use for the polymer compositions (P) developed according to this disclosure is the manufacture of shaped articles by either extrusion or molding techniques. Therefore, another aspect of the present invention relates to an article comprising the polymer composition (P).

Indeed, the outstanding balance of advantageous properties featured by the polymer compositions (C) of the present invention in connection with their high glass transition temperature, thermal stability, flame resistance, chemical resistance and melt processability, makes them particularly suitable for the manufacture, by any known processing method, of various articles. The article of the present invention may be produced by extrusion or molding techniques.

Various molding techniques may be used to form shaped articles or parts of shaped articles from the polymer composition (P). Powders, pellets, beads, flakes, reground material or other forms of the polymer composition (P) may be molded, with or without liquid or other additives, pre mixed or fed separately. The polymer composition (P) may notably be molded into a film, a sheet, or any molded article suitable for indoor and outdoor applications.

A last aspect of the present invention relates to a method for stabilizing a polymer comprising adding at least one stabilizing compound (SC) to at least one polymer. In particular, the at least one stabilizing compound (SC) may act as an acid scavenger for the at least one polymer.

The disclosure will now be illustrated with examples, which are intended to illustrate the working disclosure and not intended to take respectively to imply any limitations on the scope of the present disclosure. Modifications and variations of the present invention, related to alternative stabilizer compounds and their derivatives, will be obvious to those skilled in the art from the foregoing detailed description of the invention.

EXAMPLES

Nine compounds were synthesized using one of the two above described methods for the manufacture stabilizer compounds (SC). The effect of these nine compounds on the UV stability were tested on an aromatic polymer, namely polysulfone Udel® P-1800 (manufactured by Solvay Specialty Polymers USA, L.L.C.) by preparing solution cast films, where the compounds were present in an amount of 5 mol %.

The structural purity of all stabilizer compounds were found to be >95% using GC-MS, $^1$H NMR, $^{13}$C NMR and/or TLC. All mass spectral data was generated on a Waters Synapt G2 HDMS quadrupole time of flight (Q-TOF) operated in high resolution mode. This instrument was equipped with an atmospheric solids analysis probe (ASAP) and an atmospheric pressure chemical ionization source (APCI) that was operated in positive mode, generating ions of either M$^{-o}$, [M+H]$^+$, or [M+H$_3$O]+.

These films were formed according to the Stabilizer performance assessment description provided immediately below this section. The results obtained for these films were then compared to similar films obtained using other synthesized stabilizer compounds and commercially available stabilizer compounds widely used in the industry.

Example 1 (E1): Stabilizer Compound (A-A)

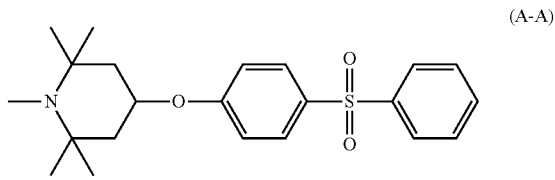 [SMILES: CN1C(C)(C)CC(Oc2ccc(S(=O)(=O)c3ccccc3)cc2)CC1(C)C]

(A-A)

Stabilizer compound (A-A), 1,2,2,6,6-pentamethyl-4-(4-(phenylsulfonyl)phenoxy) piperidine was prepared using general synthetic method 1, more specifically; potassium tert-butoxide (50 mL of a 1M solution in THF, ~0.05 mol) was combined with a stirred solution of 1,2,2,6,6-pentamethylpiperidin-4-ol (10 g, 0.0495 mol) in THF (40 mL) at 25° C. and allowed to stir for 15 min. The resultant mixture, now slightly turbid, was slowly added to a stirred solution of 1-chloro-4-(phenylsulfonyl) benzene (10 g, 0.04 mol) in THF (50 mL) at 25° C. and was then immediately heated to reflux for 72 hours. To isolate the final product, compound (A-A), the crude mixture was evaporated to dryness, recrystallized from EtOH/H$_2$O, and dried in vacuo to yield pure compound (A-A), (10.02 g, 65%) as fluffy white crystals which were >99% pure as determined via thin layer chromatography (TLC), (eluent: 1:1 hexanes/ethyl acetate) and GC-MS analysis.

The $^1$H NMR (DMSO-d6) analysis provided the following significant signals to assist in verifying the synthesis of the desired compound; δ=7.93 (m, 2H, SO2ArH), 7.85 (m, 2H, SO2ArH), 7.62 (m, 3H, ArH), 7.09 (m, 2H, O—ArH), 4.73 (m, 1H, OCH), 2.17 (s, 3H, NCH$_3$), 1.91 (m, 2H, CH$_2$), 1.39 (t, J=10.94 Hz, 2H, CH2), 1.07 (d, J=6.56 Hz, 12H, C(CH$_3$)$_2$). $^{13}$C NMR (DMSO-d6): δ=161.2 (1C, CArO), 141.9 (1C, SO$_2$CAr), 133.3 (1C, SO2CAr), 132.2 (1C, CHAr), 129.7 (2C, CHAr), 129.6 (2C, CHAr), 126.9 (2C, CHAr), 116.1 (2C, CHAr), 70.1 (1C, CHO), 54.6 (2C, CH(CH$_3$)$_2$), 45.5 (2C, CH$_2$), 32.6 (1C, NCH$_3$), 27.7 (2C, CH$_3$), 20.4 (2C, CH$_3$). HRMS (ASAP with APCI): m/z 388.1947 (M+H, calcd 388.1946). Anal. Calcd for C$_{22}$H$_{30}$NO$_3$S.

Example 2 (E2): Stabilizer Compound (A-B)

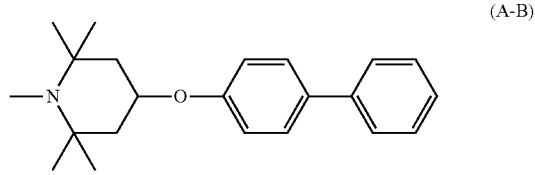 [SMILES: CN1C(C)(C)CC(Oc2ccc(-c3ccccc3)cc2)CC1(C)C]

(A-B)

Stabilizer compound (A-B), 4-(1,1'-biphenyl]-4-yloxy)-1, 2,2,6,6-pentamethylpiperidine was prepared instead by general procedure 2. The 1,2,2,6,6-pentamethylpiperidin-4-ol (15.91 g, 0.0929 mol) was added to a solution of potassium tert-butoxide (10.4 g, 0.0929 mol) dissolved in NMP (100 mL) at 25° C. (the resultant solution was red in color). Subsequently, 4-fluorobiphenyl (8.0 g, 0.0465 mol) was also dissolved in NMP (200 mL), added to the stirred reaction mixture at 25° C., heated to 100° C. for 15 h, cooled, and the crude product mixture was rotary-evaporated to dryness.

The resultant solid was then suspended in H$_2$O (500 mL), extracted repeatedly with EtOAc (3×300 mL) and the organic layers were combined, dried over MgSO$_4$, filtered, and the solvent removed in vacuo to afford a white solid that was subsequently recrystalized multiple times from EtOH. Successive recrystallization fractions were collected and each was analyzed for purity by thin layer chromatography (R$_f$=0.3, streak from baseline, in pure EtOAc). The presence of 1,2,2,6,6-pentamethylpiperidin-4-ol was visualized by using a KMnO$_4$ stain prior to combining pure fractions and drying overnight in a vacuum oven to yield compound (A-C) (11.2 g, 74.46%) as a fluffy, pearlescent white powder that was >99% pure by GC-MS.

The $^1$H NMR (DMSO-d6) analysis provided the following significant signals to assist in verifying the synthesis of the desired compound; δ=7.55 (m, 4H, ArH), 7.38 (m, 2H, ArH), 7.26 (m, 1H, ArH), 6.99 (m, 2H, OArH), 4.59 (m, 1H, OCH), 2.18 (s, 3H, NCH$_3$), 1.97 (m, 2H, CH$_2$), 1.42 (t, J=10.94 Hz, 2H, CH$_2$), 1.10 (d, J=11.67 Hz, 12H, C(CH$_3$)$_2$). $^{13}$C NMR (DMSO-d6): δ=157.5 (1C, CArO), 140.4 (1C, CAr), 133.2 (1C, CAr), 129.1 (2C, CHAr), 128.2 (2C, CHAr), 127.0 (2C, CHAr), 126.5 (1C, CHAr), 116.7 (2C, CHAr), 70.3 (1C, CHO), 55.1 (2C, CH(CH$_3$)$_2$), 46.1 (2C, CH$_2$), 33.0 (1C, NCH$_3$), 28.2 (2C, CH$_3$), 21.4 (2C, CH$_3$). HRMS (ASAP with APCI): m/z 324.2356 (M+H, calcd 324.2327). Anal. Calcd for C$_{22}$H$_{30}$NO.

Example 3 (E3): Stabilizer Compound (A-C)

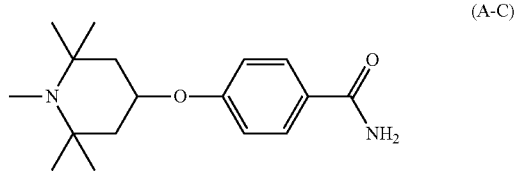 [SMILES: CN1C(C)(C)CC(Oc2ccc(C(N)=O)cc2)CC1(C)C]

(A-C)

Stabilizer compound (A-C), 4-((1,2,2,6,6-pentamethylpiperidin-4-yl)oxy) benzamide was prepared according to general procedure 2. A solution of 1,2,2,6,6-pentamethylpiperidin-4-ol (37.33 g, 0.217 mol) in NMP (200 mL) was slowly added to a the stirred solution of KOtBu (24.35 g, 0.260 mol) in NMP (200 mL) resulting in a reaction that caused a color change to purple and the resultant mixture was allowed to stir at room temperature for 15 minutes to generate the potassium salt nucleophile. Subsequently, 4-fluorobenzonitrile (12 g, 0.099 mol) was added in one step and the reaction was then heated to 100° C. under nitrogen for 48 hours. Extraction was performed as detailed above, but in this case, combined organic layers were dried over anhydrous MgSO$_4$, filtered, and the solvent was removed under reduced pressure resulting in providing a dark brown oil which solidified overnight. To isolate the desired product a fractional distillation on a high vacuum line was performed (vacuum distillation). The first fraction, comprised primarily of 1,2,2,6,6-pentamethylpiperidin-4-ol, crystallized in the distillation apparatus as fine needles. This fraction distilled at 75° C. and 1 torr (oil bath set to 140° C.). The second fraction, distilled at 85° C. and 0.8 torr (oil bath set to 160° C.) resulting in a colorless oil. A third, very high boiling fraction (temperature set=220° C.) was isolated as a yellow, transparent solid. This third fraction was dissolved in acetone and all insoluble solids were subsequently filtered off. The acetone soluble fractions were rotovapped to dryness and subsequently recrystallized from tolune to afford compound VI (5.0 g, 18.5%) as a white powder that is >97% pure by GC-MS.

The $^1$H NMR (DMSO-d6) analysis provided the following significant signals to assist in verifying the synthesis of the desired compound: δ=7.77 (m, 3H, C=ONH$_2$ArH, C=ONH$_2$), 7.14 (bs, 1H, C=ONH$_2$), 6.90 (m, 2H, OArH), 4.67 (m, 1H, OCH), 2.14 (s, 3H, NCH$_3$), 1.89 (m, 2H, CH$_2$), 1.36 (t, J=X Hz, 2H, CH$_2$), 1.06 (d, J=X Hz, 12H, C(CH$_3$)$_2$). $^{13}$C NMR (DMSO-d6): δ=167.8 (1C, C=ONH$_2$), 160.0 (1C, OC$_{Ar}$), 129.8 (2C, CH$_{Ar}$), 126.7 (2C,CH$_{Ar}$), 115.2 (2C, CH$_A$), 69.7 (1C, CHO), 55.1 (2C, CH(CH$_3$)$_2$), 46.2 (2C, CH$_2$), 33.1 (1C, NCH$_3$), 28.1 (2C, CH$_3$), 20.8 (2C, CH$_3$). HRMS (ASAP with APCI): m/z 291.2096 (M+H, calcd. 291.2073). Anal. Calcd for C$_{17}$H$_{27}$N$_2$O$_2$.

Example 4 (E4): Stabilizer Compound (B-A)

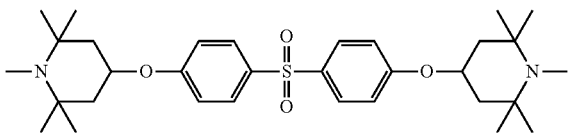

(B-A)

Stabilizer compound (B-A); 4,4'-((sulfonylbis(4,1-phenylene))bis(oxy))bis(1,2,2,6,6-pentamethylpiperidine) was prepared according to general procedure 1. As before, the stirred solution of 1,2,2,6,6-pentamethylpiperidin-4-ol (26.24 g, 0.153 mol) in THF (200 mL) was prepared and within fifteen minutes a solution of 4,4'-dichloro diphenyl sulfone (20 g, 0.0696 mol) was added to the stirred reaction vessel, which was heated, refluxed under N$_2$ for 72 hours, and followed by recrystallization from a mixture of EtOH/H$_2$O 90:10 yielding compound VII (31.71 g, 81.8%) as a white fluffy solid.

The $^1$H NMR (DMSO-d6) analysis provided the following significant signals to assist in verifying the synthesis of the desired compound: δ=7.76 (m, 4H, SO$_2$ArH), 7.04 (m, 4H, SO$_2$ArH), 4.65 (m, 2H, OCH), 2.17 (s, 6H, NCH$_3$), 1.91 (m, 4H, CH$_2$), 1.41 (t, J=11.67 Hz, 4H, CH$_2$), 1.05 (d, J=10.2 Hz, 24H, C(CH$_3$)$_2$). $^{13}$C NMR (DMSO-d6): δ=161.5 (2C, CArO), 134.0 (2C, SO$_2$CAr), 129.7 (4C, SO$_2$CAr), 116.5 (4C, OCHAr), 70.9 (2C, CHO), 55.1 (4C, CH(CH$_3$)$_2$), 46.2 (4C, CH$_2$), 32.8 (2C, NCH$_3$), 28.1 (4C, CH$_3$), 21.4 (4C, CH$_3$). HRMS (ASAP with APCI): m/z 557.3464 (M+H, calcd. 557.3413). Anal. Calcd for C$_{32}$H$_{49}$N$_2$O$_4$S.

Example 5 (E5): Stabilizer Compound (B-B)

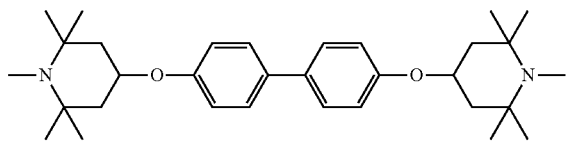

(B-B)

Stabilizer compound (B-C), 4,4'-bis((1,2,2,6,6-pentamethylpiperidin-4-yl)oxy)-1,1'-biphenyl, was prepared according to general procedure 2. The 1,2,2,6,6-pentamethylpiperidin-4-ol (19.81 g, 0.1157 mol) solution was followed by addition of the 4-4'-difluorobiphenyl (10.0 g, 0.0526 mol) solution as before and heated to 100° C. for 72 hours, cooled, and the resultant solid isolated. The solid was purified according to the same procedure used for examples 3,4, and 6, ultimately providing compound (B-C) (9.80 g, 37%) which appeared as a fluffy, pearlescent white powder that was >95% pure as determined by GC-MS The $^1$H NMR (DMSO-d6) analysis provided the following significant signals to assist in verifying the synthesis of the desired compound: δ=7.49 (m, 4H, ArH), 6.99 (m, 4H, ArH), 4.60 (m, 2H, OCH), 2.23 (s, 6H, NCH$_3$), 1.96 (m, 4H, CH$_2$), 1.46 (t, J=11.67 Hz, 4H, CH$_2$), 1.15-1.11 (d, J=13.85 Hz, 24H, C(CH$_3$)$_2$). $^{13}$C NMR (DMSO-d6): δ=156.9 (2C, CArO), 133.0 (2C, CAr), 127.6 (4C, CAr), 116.7 (4C, CHAr), 70.2 (2C, CHO), 55.1 (4C, CH$_2$), 46.7 (4C, CH$_2$), 33.0 (2C, NCH$_3$), 28.2 (4C, CH$_3$), 21.4 (4C, CH$_3$). HRMS (ASAP with APCI): m/z 493.3844 (M+H, calcd. 493.3794). Anal. Calcd for C$_{32}$H$_{49}$N$_2$O$_2$.

Comparative Example 1 (CE1): Stabilizer Compound (C-A)

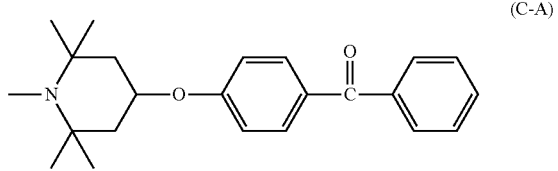 [SMILES: CN1C(C)(C)CC(Oc2ccc(C(=O)c3ccccc3)cc2)CC1(C)C]

(C-A)

Stabilizer compound (C-A),(4-((1,2,2,6,6-pentamethylpiperidin-4-yl)oxy)phenyl)(phenyl) methanonealso was prepared according to general procedure 1, with the exception that the potassium tert-butoxide stirred solution of 1,2,2,6,6-pentamethylpiperidin-4-ol was slowly added to a stirred solution of 4-fluorobenzophenone and refluxed as above. The crude mixture was isolated in the same manner as well, and the pure compound A-B (12.53 g, 72% yield) also appeared as pure (>99%) white crystals.

To confirm the (C-A) compound was isolated, again $^1$H NMR (DMSO-d6) analysis was performed as above with the following results; δ=7.70 (m, 2H, C═OArH), 7.66 (m, 2H, C═OArH), 7.59 (m, 1H, ArH), 7.52 (m, 2H, ArH), 7.03 (m, 2H, OArH), 4.71 (m, 1H, OCH), 2.18 (s, 3H, NCH$_3$), 1.97 (m, 2H, CH$_2$), 1.44 (t, J=11.67 Hz, 2H, CH$_2$), 1.10 (d, J=9.48 Hz, 12H, C(CH$_3$)$_2$). $^{13}$C NMR (DMSO-d6): δ=194.6 (1C, C═O), 161.6 (1C, CArO), 138.4 (1C, C═OCAr), 132.5 (1C, C═OCAr), 132.2 (1C, CHAr), 129.8 (2C, CHAr), 129.4 (2C, CHAr), 128.7 (2C, CHAr), 115.6 (2C, CHAr), 70.5 (1C, CHO), 55.1 (2C, CH(CH$_3$)$_2$), 46.3 (2C, CH2), 33.0 (1C, NCH$_3$), 28.1 (2C, CH$_3$), 21.2 (2C, CH$_3$). HRMS (ASAP with APCIEI): m/z) 352.2269 (M+H, calcd 352.2277). Anal. Calcd for C$_{23}$H$_{29}$NO$_2$.

Comparative Example 2 (CE2): Stabilizer Compound (C-B)

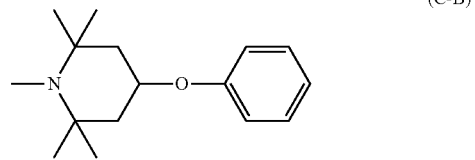

(C-B)

Stabilizer compound (C-B), 1,2,2,6,6-pentamethyl-4-phenoxypiperidine was identically prepared according to general procedure 2 with the exception that in this case, 4-fluorobenzene (12.49 g, 0.130 mol) was added dropwise to the stirred solution of 1,2,2,6,6-pentamethylpiperidin-4-ol (44.56 g, 0.260 mol) and upon complete addition, the reaction mixture was heated to 85° C. for 72 hours. The resultant product was isolated, and further purified via fractional distillation (85° C., 0.8 torr) to yield compound A-D (17.47 g, 54%), as a colorless oil that was >98% pure as determined by TLC (eluent: EtOAc, Rf=0.4) and GC-MS.

The $^1$H NMR (DMSO-d6) analysis provided the following significant signals to assist in verifying the synthesis of the desired compound; δ=7.23 (m, 2H, OArH), 6.86 (m, 3H, ArH), 4.55 (m, 1H, OCH), 2.15 (s, 3H, NCH3), 1.90 (m, 2H, CH$_2$), 1.35 (t, J=11.67 Hz, 2H, CH$_2$), 1.04 (d, J=10.94 Hz, 12H, C(CH$_3$)$_2$). $^{13}$C NMR (DMSO-d6): δ=157.6 (1C, CArO), 129.9 (2C, CHAr), 120.7 (1C, CHAr), 115.9 (2C, CHAr), 69.3 (1C, CHO), 55.0 (2C, CH(CH$_3$)$_2$), 46.4 (2C, CH$_2$), 33.2 (1C, NCH$_3$), 28.1 (2C, CH$_3$), 20.8 (2C, CH$_3$). HRMS (ASAP with APCI): m/z 248.2034 (M+H, calcd 248.2014). Anal. Calcd for C$_{16}$H$_{26}$NO).

Comparative Example 5 (CE5): Stabilizer Compound (C-C)

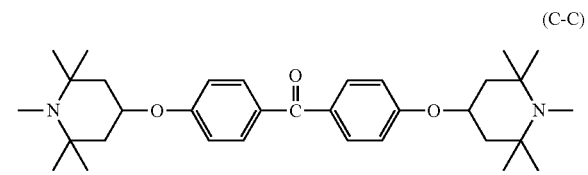

(C-C)

Stabilizer compound (C-C), bis(4-((1,2,2,6,6-pentamethylpiperidin-4-yl)oxy)phenyl)methanone, was also prepared according to general procedure 1 using a stirred solution of 1,2,2,6,6-pentamethylpiperidin-4-ol (34.55 g, 0.20 mol) in THF (200 mL). Fifteen minutes later, a solution of difluorobenzophenone (20 g, 0.0917 mol) was added during stirring, refluxed, and recrystallized from a mixture of EtOH/H$_2$O 90:10 resulting in compound B-B (41.64 g, 87.1%) appearing as a white fluffy solid.

The $^1$H NMR (DMSO-d6) analysis provided the following significant signals to assist in verifying the synthesis of the desired compound: δ=7.69 (m, 4H, C═OArH), 7.05 (m, 4H, C═OArH), 4.72 (m, 2H, OCH), 2.23 (s, 6H, NCH$_3$), 1.99 (m, 4H, CH$_2$), 1.50 (t, J=11.67 Hz, 4H, CH$_2$), 1.15 (d, J=10.21 Hz, 24H, C(CH$_3$)$_2$). $^{13}$C NMR (DMSO-d6): δ=193.3 (1C, C═O), 161.2 (2C, CArO), 132.1 (4C, CHAr), 130.6 (2C, CAr), 115.6 (4C, OCHAr), 70.6 (2C, CHO), 55.1 (4C, CH(CH$_3$)$_2$), 46.4 (4C, CH$_2$), 32.9 (2C, NCH$_3$), 28.2 (4C, CH$_3$), 21.4 (4C, CH$_3$). HRMS (ASAP with APCI): m/z 521.3794 (M+H, calcd. 521.3743). Anal. Calcd for C$_{33}$H$_{49}$N$_2$O$_3$.

Comparative Example 6 (CE6): Stabilizer Compound (C-D)

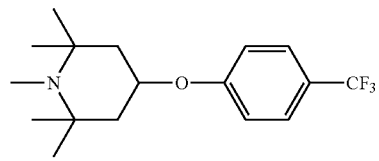 [SMILES: CN1C(C)(C)CC(Oc2ccc(C(F)(F)F)cc2)CC1(C)C]

Stabilizer compound (C-D), 1,2,2,6,6-pentamethyl-4-((4trifluoromethyl)phenoxy)piperidine, was synthesized according to general procedure 1 using 2,2,6,6-pentamethylpiperidin-4-ol (12.52 g, 0.073 mol) and Potassium tert-butoxide (73 mL of a 1M solution in THF, 0.073 mol) in THF (40 mL) and 4-fluorobenzotrifluoride (10 g, 0.061 mol) in THF (50 mL). The final product was purified via multiple vacuum distillations (100-110° C. at 1 torr) to yield the desired compound (A-E) (11.2 g, 58% yield) as a colorless oil that was 97% pure as determined by GC-MS. For this compound, TLC analysis showed a high degree of conversion to the desired product (eluent: EtOAc/Hex 1:1, Rf=0.7).

The $^1$H NMR (DMSO-d6) analysis provided the following significant signals to assist in verifying the synthesis of the desired compound: δ=7.62 (m, 2H, CF$_3$ArH), 7.12 (m, 2H, OArH), 4.75 (m, 1H, OCH), 2.19 (s, 3H, NCH$_3$), 1.95 (m, 2H, CH$_2$), 1.41 (t, J=10.95 Hz, 2H, CH$_2$), 1.09 (d, J=6.57 Hz, 12H, C(CH$_3$)$_2$). $^{13}$C NMR (DMSO-d6): δ=160.5 (1C, CArO), 127.4 (4C, CF$_3$, CF$_3$CAr, CHAr), 116.2 (2C, CHAr), 70.1 (1C, CHO), 55.1 (2C, CH(CH$_3$)$_2$), 46.0 (2C, CH$_2$), 33.1 (1C, NCH$_3$), 28.1 (2C, CH$_3$), 20.8 (2C, CH$_3$). HRMS (ASAP with APCI): m/z 316.1918 (M+H, calcd. 316.1888). Anal. Calcd for C$_{17}$H$_{25}$F$_3$NO.

Table 1 below provides a summary of the nine stabilizer compounds prepared including a listing of the general synthesis methods utilized in making them.

TABLE 1

Stabilizer compounds prepared by general procedures 1 and 2

| EXAMPLE | STABILIZER STRUCTURE | GENERAL PROCEDURE[1,2] | YIELD[3] |
|---|---|---|---|
| E1 (A-A) | | 1 | 65% |
| E2 (A-B) | | 2 | 74.4% |
| E3 (A-C) | | 2 | 18.5% |
| E4 (B-A) | | 1 | 81.8% |
| E5 (B-B) | | 2 | 37% |
| CE1 (C-A) | | 1 | 72% |

TABLE 1-continued

Stabilizer compounds prepared by general procedures 1 and 2

| EXAMPLE | STABILIZER STRUCTURE | GENERAL PROCEDURE[1,2] | YIELD[3] |
|---|---|---|---|
| CE2 (C-B) | | 2 | 54% |
| CE5 (C-C) | | 1 | 87.1% |
| CE6 (C-D) | | 1 | 58% |

[1]General Procedure 1: Base:Potassium tert-butoxide, Solvent: THF, Reaction Temperature: 66° C., Reaction Time 16 h
[2]General Procedure 2: Base:Potassium tert-butoxide, Solvent: NMP, Reaction Temperature: 100° C., Reaction Time 16 h
[3]All Stabilizer Compounds (SC) were reacted with the yields provided and obtained at >95% purity Stabilizer Performance Assessment To examine the efficacy of the stabilizer compounds in retarding the rate of UV degradation in aromatic polymers, the aromatic polymer polysulfone manufactured by Solvay Specialty Polymers USA, L.L.C. under the tradename UDEL® polysulfone P1800 was solution blended with stabilizer compounds E1, E2 and E4 (as summarized in Table 2) at 5 mol % loading. This was accomplished by first dissolving the stabilizer compound and polymer in dimethyl formamide (DMF) to prepare a 23 wt. % solution (percent total solids) followed by film casting onto a glass plate pre-heated to 70 C using a 15 mil side of a square applicator (BYK Gardener). The resulting 4"×4"×50 micron thick film was dried (on a glass plate) using a vacuum oven (120 C, <−25 mmHg) for 48 h, at which point the film was removed from the glass substrate using a razor blade. The free-standing film was then cut into 10 mm×100 mm×50 micron strips using a precision trammel cutter and mounted onto an aluminum frame designed for use in an Atlas ci4000 Xenon weather-o-meter. All films were checked for removal of residual solvent using FT-IR (the carbonyl band for DMF at 1680 cm-1 prior to UV exposure).

The same procedure was followed for the comparative stabilizer compounds CE1, CE3 and CE4 allowing the comparison between the stabilizers synthesized and two commercially available light stabilizers (i.e. Chiguard 770 and Chiguard 353, commercially available from Chitec® Technology, respectively called CE3 and CE4).

All weathering experiments were carried out in 24 hour increments for up to 5 days using the same weather-o-meter which was also further equipped with a Type "S" borosilicate inner filter and a soda lime outer filter. The cut-off filters eliminated all wavelengths>340 nm. All weathering cycles were set for an irradiance of 0.30 w/m², with a panel temperature of 55° C. a chamber temperature of 38° C., and a relative humidity of 55%. All other variables were controlled in accordance with ASTM G155-4. Following exposure to UV, each film was subsequently placed in a UV Vis spectrophotometer set to transmission mode and the UV-Vis spectra was collected at λ=350 nm.

Table 2 summarizes the changes in transmission after UV ageing (exposure) in the same weather-o-meter for the mono-substituted piperidin-ol stabilizer compounds (A-A), (A-B), and (A-C) as well as for the comparative examples CE1 (C-A), and piperidine-based commercial compounds CE3 and CE4 (HALS).

Table 3 summarizes the change in glass transition temperatures (Tg), which were measured by Differential scanning calorimetry (DSC) performed under nitrogen using a TA instruments DSC Q10 differential scanning calorimeter. The temperature program provided two sequential heating and cooling cycles that were carried out between 25° C. and 225° C. at a rate of 20° C./min. All glass transition temperatures were determined using TA Thermal Advantage and Universal Analysis software and were made using the second heat cycle.

Table 4 summarizes the change in transmission after UV ageing (exposure) in the same weather-o-meter for the bis-substituted stabilizer compounds (B-A) (E4), and (B-B) (E5) as well as for the comparative examples CE5 (compound (C-C)).

TABLE 2

Transmission (%) vs UV exposure time (days) of Udel® PSU and its blends with 5 mol % monosubstituted stabilizers

| UV Ageing Time (days) | Control No Stabilizer | UDEL® + E1 | UDEL® + E2 | UDEL® + E3 | UDEL® + CE1 | UDEL® + CE3 | UDEL® + CE4 |
|---|---|---|---|---|---|---|---|
| 0 | 80.70 | 80.70 | 80.70 | 80.70 | 80.70 | 80.70 | 80.70 |
| 1 | 36.55 | 48.96 | 51.88 | 49.88 | 37.06 | 60.78 | 51.38 |
| 2 | 30.21 | 40.76 | 42.02 | 40.32 | 29.24 | 42.16 | 43.94 |
| 3 | 24.00 | 34.59 | 36.23 | 35.37 | 24.27 | 38.49 | 37.61 |
| 4 | 23.26 | 30.20 | 31.69 | 30.68 | 17.96 | 35.01 | 35.05 |
| 5 | 16.33 | 27.48 | 29.59 | 29.43 | 17.69 | 28.67 | 27.75 |

TABLE 3

Glass transition temperatures Udel ® PSU and its blends with 5 mol % stabilizers

| | UDEL® Control | UDEL® + E1 | UDEL® + E2 | UDEL® + E4 | UDEL® + E5 | UDEL® + CE1 | UDEL® + CE3 | UDEL® + CE4 | UDEL® + CE5 |
|---|---|---|---|---|---|---|---|---|---|
| Tg (° C.) | 185 | 172 | 167 | 176 | 165 | 168 | 152 | 156 | 176 |
| Δ Tg (° C.) | N/A | −13 | −18 | −9 | −20 | −17 | −35.5 | −31.83 | −9 |

TABLE 4

Transmission (%) vs UV exposure time (days) of Udel® PSU and its blends with 5 mol % disubstituted stabilizers

| UV Ageing Time (days) | Control – No Stabilizer | UDEL® + E4 | UDEL® + E5 | UDEL® + CE5 |
|---|---|---|---|---|
| 0 | 80.70 | 80.70 | 80.70 | 80.70 |
| 1 | 36.55 | 46.47 | 48.23 | 38.80 |
| 2 | 30.21 | 38.02 | 39.18 | 29.99 |
| 3 | 24.00 | 32.90 | 33.48 | 27.16 |
| 4 | 23.26 | 27.13 | 28.57 | 21.40 |
| 5 | 16.33 | 25.78 | 27.19 | 19.88 |

Compound (C-D) of CE6 presented a very low thermal stability. The temperature at which 10% wt. loss was observed by thermal gravimetric analysis (TGA) for compound (A-C) was 132° C. and would therefore not be suitable to be used at the processing temperatures of commodity polymers, let alone the high processing temperatures of high performance aromatic polymers.

Now, when analyzing the transmission data of tables 2 and 4, it appears that the presence of stabilizer compounds E1, E2, E3, CE3, CE4, E4 and E5 greatly improves the behavior of UDEL® PSU after 5 days exposure to UV, bringing the transmission values to at least 25%, compared to the 16% obtained for the unstabilized UDEL® PSU control.

However, these results are further evaluated with the data provided on table 3 on the Tg of the films. It is important that the incorporation of additives/stabilizers do not reduce too much the Tg of the polymer. It is interesting to note that the Tg obtained on the films containing the commercially available stabilizers CE3 and CE4 dropped to very low and unacceptable Tg values with a ΔTg compared to the Tg of the UDEL® polysulfone alone of at least 31° C. Surprisingly, the ketone structures of CE1 and CE5, which contain benzophenone moieties, did not impart increased UV stability.

Should the disclosure of any patents, patent applications, and publications which are incorporated herein by reference conflict with the description of the present application to the extent that it may render a term unclear, the present description shall take precedence.

The invention claimed is:
1. Stabilizer compounds (SC) of formula (I) or formula (II):

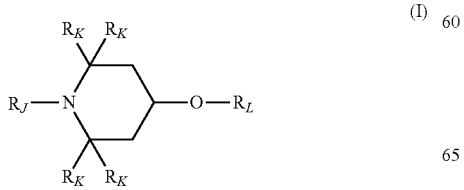

(I)

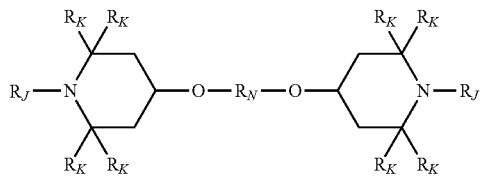

(II)

wherein $R_J$ is selected from the group consisting of —H, —CH$_3$, —CH$_2$CH$_3$, —OCH$_3$, and —OCH$_2$CH$_3$, and wherein each of $R_K$, equal or different from each other and from $R_J$, is selected from the group consisting of:

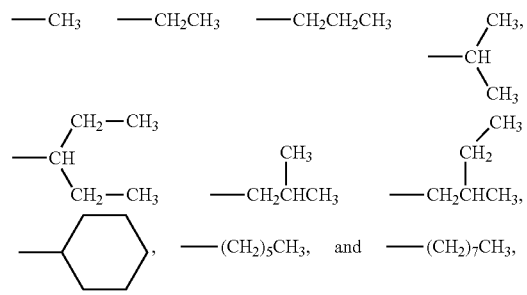

wherein $R_L$ is a monovalent substituent of general formula (Y-I):

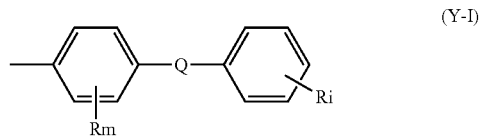

(Y-I)

wherein Ri and Rm are the same or different from each other and are independently selected from the group consisting of H,
and alkyl groups of formula —CH$_3$, —CH$_2$OCH$_3$ and

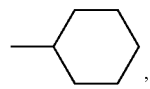

and
wherein Ri is either in an ortho, meta or para position, and wherein Rm is either in an ortho or meta position, and wherein Q is —SO$_2$—, and wherein $R_N$ is a divalent substituent selected from the group consisting of general formula (Z-I):

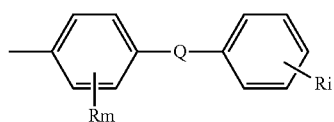
(Z-I)

wherein Ri and Rm are the same or different from each other and are independently selected from the group consisting of —H, alkyl groups of formula —CH₃, —CH₂OCH₃ and

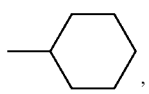

wherein Ri and Rm are independently either in an ortho or meta position, and wherein Q is —SO₂—.

2. The stabilizer compounds (SC) of formula (I) of claim 1, wherein said stabilizer compound (SC) is:

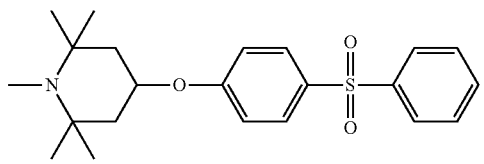
(A-A)

3. The stabilizer compounds (SC) of formula (H) of claim 1, wherein said stabilizer compound (SC) is:

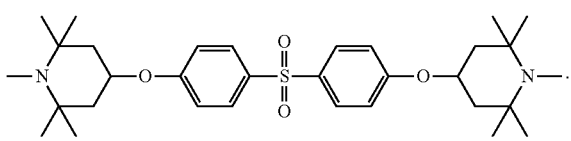
(B-A)

4. The stabilizer compound (SC) according to claim 1, wherein Rm is —H.

5. A method for the manufacture of the stabilizer compound of formula (I) of claim 1, comprising the step of reacting compounds of formulae (III) and (IV) together in the presence of a base;

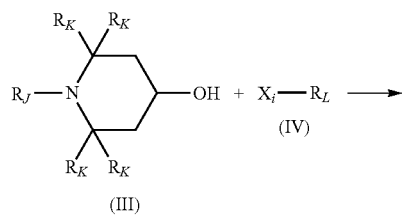
(III)

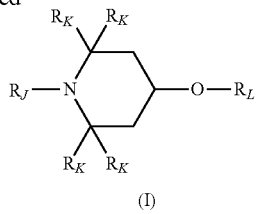
(I)

wherein Xi is a halogen selected from the group consisting of chlorine, fluorine, bromine, and iodine, and wherein $R_J$, $R_K$, $R_L$ are as defined in claim 1 for formula (I).

6. A method for the manufacture of the stabilizer compound of formula (II) of claim 1, comprising the step of reacting compounds of formulae (111) and (IV) together in the presence of a base:

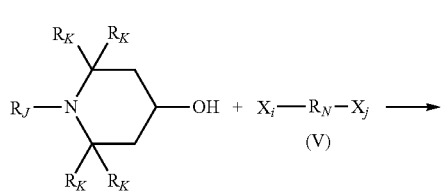
(V)
(III)

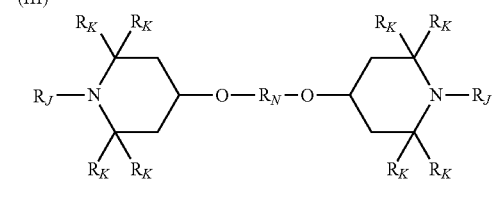
(II)

wherein Xi or Xj are the same or independently selected halogens from the group consisting of chlorine, fluorine, bromine, and iodine, and wherein $R_J$, $R_K$, $R_N$ are as defined in claim 1 for formula (II).

7. The method of claim 6, wherein the reaction is carried out in a polar aprotic solvent.

8. The method of claim 7, wherein the polar aprotic solvent is tetrahydrofuran and the reaction is carried out at a temperature of between 25° C. and 66° C.

9. The method of claim 7, wherein the polar aprotic solvent is N-methylpyrrolidone and the reaction is carried out at a temperature of between 25° C. and 204° C.

10. A polymer composition (P), comprising at least one stabilizer compound (SC) of claim 1 and at least one polymer selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene, styrene acrylonitrile, acrylate styrene acrylonitrile, cellulosic acetate butyrate, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

11. The polymer composition (P) of claim 10, wherein the at least one polymer is selected from the group consisting of polyketones, poly(etherketone)s, and poly(ethersulfone)s.

12. The polymer composition (P) of claim 10, wherein it further comprises at least another ingredient selected from the group consisting of dyes, pigments, fillers, UV stabilizers, light stabilizers, optical brighteners.

13. A method for stabilizing a polymer comprising adding at least one stabilizing compound (SC) of claim 1 to at least one polymer.

14. The method of claim 13, where the at least one stabilizing compound (SC) acts as an acid scavenger for the at least one polymer.

15. An article comprising the polymer composition (P) of claim 10.

\* \* \* \* \*